(12) United States Patent
Bossenmaier et al.

(10) Patent No.: US 7,432,291 B2
(45) Date of Patent: Oct. 7, 2008

(54) ETHER DERIVATIVES

(75) Inventors: Birgit Bossenmaier, Seefeld (DE); Walter-Gunar Friebe, Mannheim (DE); Thomas Friess, Planegg (DE); Ulrike Reiff, Penzberg (DE); Edgar Voss, Bichl (DE)

(73) Assignee: Hoffman-La Roche Inc., Nutley, NJ (US)

( * ) Notice: Subject to any disclaimer, the term of this patent is extended or adjusted under 35 U.S.C. 154(b) by 516 days.

(21) Appl. No.: 11/083,176

(22) Filed: Mar. 17, 2005

(65) Prior Publication Data

US 2005/0209290 A1      Sep. 22, 2005

(30) Foreign Application Priority Data

Mar. 18, 2004   (EP) ................... 04006509

(51) Int. Cl.
  *A61K 31/41*   (2006.01)
  *C07D 249/04*  (2006.01)

(52) U.S. Cl. ...................... 514/359; 548/255

(58) Field of Classification Search ............... 514/359; 548/255
See application file for complete search history.

(56) References Cited

U.S. PATENT DOCUMENTS

| | | | |
|---|---|---|---|
| 7,163,953 B2* | 1/2007 | Bossenmaier et al. | 514/374 |
| 7,235,574 B2* | 6/2007 | Bossenmaier et al. | 514/374 |

FOREIGN PATENT DOCUMENTS

| | | |
|---|---|---|
| EP | 1270571 | 1/2003 |
| WO | WO 98/03505 | 1/1998 |
| WO | WO 01/77107 | 10/2001 |
| WO | WO 03/031442 | 4/2003 |
| WO | WO 03/059907 | 7/2003 |

OTHER PUBLICATIONS

Copending U.S. Appl. No. 11/073,065.*
Wilks et al., Progress in Growth Factor Research, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).
Bastin et al., Organic Proc. Res. Dev., 4, pp. 427-435 (2000).

* cited by examiner

*Primary Examiner*—Rei-tsang Shiao
*Assistant Examiner*—Susannah Chung
(74) *Attorney, Agent, or Firm*—George W. Johnston; Patricia S. Rocha-Tramaloni; Gene J. Yao

(57) ABSTRACT

The present invention provides the compounds of formula (I)

formula (I)

their pharmaceutically acceptable salts or esters, enantiomeric forms, diastereoisomers and racemates, the preparation of the above-mentioned compounds, compositions containing them and their manufacture, as well as the use of the above-mentioned compounds in the control or prevention of illnesses such as cancer.

17 Claims, No Drawings

ETHER DERIVATIVES

PRIORITY TO RELATED APPLICATIONS

This application claims the benefit of European Application No. 04006509.6, filed Mar. 18, 2004, which is hereby incorporated herein by reference in its entirety.

FIELD OF THE INVENTION

The present invention relates to novel ether derivatives, to a process for their manufacture, pharmaceutical compositions containing them and their manufacture as well as the use of these compounds as pharmaceutically active agents for the prevention or treatment of cancer.

BACKGROUND OF THE INVENTION

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, Ick). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118-121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (suppl. 1) (2002) 17-24).

Some substituted oxazoles are known in the art. WO 98/03505, EP 1 270 571, WO 01/77107, WO 03/031442 and WO 03/059907 disclose related heterocyclic compounds as -tyrosine kinase inhibitors.

However there remains a need for new compounds with improved therapeutic properties, such as enhanced activity, decreased toxicity, better solubility and improved pharmacokinetic profile, to name only a few.

SUMMARY OF THE INVENTION

The present invention relates to a compound of the general formula I,

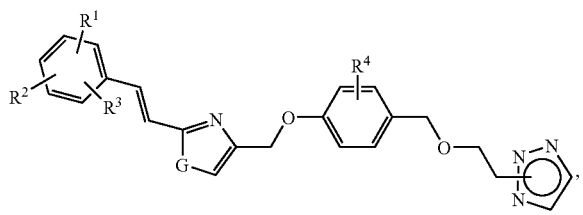

formula (I)

wherein:
G is oxygen or sulfur;
$R^4$ is selected from the group consisting of:
  (a) hydrogen;
  (b) $C_1$-$C_3$ alkyl;
  (c) $C_1$-$C_3$ alkoxy; and
  (d) halogen;
and, either:
(A) $R^1$ is selected from the group consisting of:
  (a) —O-alkyl, wherein the alkyl group is optionally substituted with one or more halogen atoms;
  (b) —S-alkyl, wherein the alkyl group is optionally substituted with one or more halogen atoms; and
  (c) —NH-alkyl, wherein the alkyl group is optionally substituted with one or more halogen atoms;
$R^2$ is hydrogen or halogen; and
$R^3$ is hydrogen;
or, alternatively,
(B)
$R^1$ and $R^2$, together with the carbon atoms to which they are attached, form a 5 or 6 membered heterocyclic ring, optionally substituted with one or more halogen atoms, and $R^3$ is hydrogen or halogen;
or a pharmaceutically acceptable salt or ester thereof.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signaling pathway and therefore possess anti-proliferative activity. The present invention provides the compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably from 1 or 2, carbon atoms, such as methyl, ethyl, n-propyl, isopropyl, n-butyl, 2-butyl, t-butyl. Said "alkyl" group is optionally substituted with one or more halogen atoms, preferably fluorine. Examples are difluoromethyl, trifluoromethyl, 2,2,2-trifluoroethyl, perfluorethyl and the like.

As used herein, the term "halogen" encompasses fluorine, chlorine, bromine and iodine. In certain preferred embodiments the halogen is fluorine.

As used herein, the term a "5 or 6 membered heterocyclic ring" means a monocyclic saturated or unsaturated hydrocarbon with 5 or 6 ring atoms of which 1 or 2 atoms are replaced by S, N or O, preferably N or O, and the remaining carbon-atoms, where possible, are optionally substituted one or more times with halogen, preferably fluorine. Preferably said "5 or 6 membered heterocyclic ring" is formed by $R^1$ and $R^2$ being located on two adjacent carbon-atoms of the phenyl ring to which they are attached. Examples of a "5 or 6 membered heterocyclic ring", including the phenyl ring to which it is attached, are benzo[1,3]dioxole, 2,2-difluoro-benzo[1,3]dioxole, 1H-benzimidazole, 2,3-dihydro-benzo[1,4]dioxine, 3,4-dihydro-2H-benzo[1,4]oxazine and the like.

As used herein, when referring to the receptor tyrosine kinases of the HER-family like HER-2 and EGFR (HER-1), the acronym "HER" refers to human epidermal receptor and the acryonym "EGFR" refers to epidermal growth factor receptor.

As used herein, "DMEM" means Dulbecco's Modified Eagle Medium.

As used herein, "FCS" means Fetal Calf Serum.

As used herein, "EGTA" means Ethylene glycol-bis(2-aminoethylether)-N,N,N',N'-tetraacetic acid.

As used herein, "Hepes" means 4-(2-Hydroxyethyl)-1-piperazineethanesulfonic acid.

As used herein, "PMSF" means Phenylmethylsulfonyl fluoride.

As used herein, "Aprotinin" refers to a naturally occurring protein that is obtained and purified from cow's lungs.

As used herein, "Orthovanadate" refers to $Na_3VO_4$.

As used herein, "DMSO" means N,N-dimethylsulfoxide.

As used herein, the "pY 1248 in HER2" refers to the phosphorylated tyrosine residue 1248 of human epidermal receptor 2.

As used herein, "NSCLC cells" (e.g. QG56, A549, Calu-3) refers to Non-Small-Cell Lung Cancer cells.

As used herein, "NCI" refers to the National Cancer Institute.

As used herein, "Lactose Anhydrous DTG" refers to anhydrous lactose in direct tabletting grade.

As used herein, the term "r.t." refers to room temperature.

As used herein, the term "DMF" refers to N,N-dimethyl formamide.

As used herein, in relation to mass spectrometry (MS) the term "ESI+" refers to positive electrospray ionization mode and the term "M+" refers to the positive molecular mass ion peak of the ionized molecule.

As used herein, in relation to nuclear magnetic resonance (NMR) the term "$D_6$-DMSO" refers to deuterated N,N-dimethylsulfoxide.

As used herein, "THF" means tetrahydrofuran.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalene-sulfonic acid, naphthalenedisulfonic acid, methanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Bastin, R. J. et al, Organic Proc. Res. Dev. 4 (2000) 427-435.

Preferred are the pharmaceutically acceptable salts, which are formed with p-toluenesulfonic acid, naphthalenesulfonic acid, naphthalenedisulfonic acid, methanesulfonic acid and hydrochloric acid.

Preferred substituents of $R^1$ are methoxy, difluoromethoxy, trifluoromethoxy and trifluoromethylsulfanyl.

When "$R^1$ and $R^2$ together with the carbon atoms to which they are attached form a 5 or 6 membered heterocyclic ring", the resulting bicyclic ring system, including the phenyl moiety to which $R^1$ and $R^2$ are attached is preferably 2,2-Difluoro-benzo[1,3]dioxolyl.

A preferred embodiment are the compounds of formula I, wherein G is oxygen and the remaining substituents have the significance given above.

Another preferred embodiment are the compounds of formula I, wherein G is sulfur and the remaining substituents have the significance given above.

Still a preferred embodiment of the invention are the compounds of formula I, wherein:

$R^1$ is —O—$CF_3$; —O—$CHF_2$ or —S—$CF_3$;

$R^2$, $R^3$ and $R^4$ are all hydrogen; and

G is oxygen; and pharmaceutically acceptable salts or esters thereof

Such compounds are for example:

1-[2-(4-{2-[2-(E)-(4-Trifluoromethylsulfanyl-phenyl)-vinyl]-oxazol-4-ylmethoxy}-benzyloxy)-ethyl]-1H-[1,2,3]triazole;

2-[2-(4-{2-[2-(E)-(4-Trifluoromethoxy-phenyl)-vinyl]-oxazol-4-ylmethoxy}-benzyloxy)-ethyl]-2H-[1,2,3]triazole; and 4-[2-(4-{2-[2-(E)-(4-Trifluoromethoxy-phenyl)-vinyl]-oxazol-4-ylmethoxy}-benzyloxy)-ethyl]-1H-[1,2,3]-triazole.

Such pharmaceutically acceptable salts are for example:

1-[2-(4-{2-[2-(E)-(4-Trifluoromethoxy-phenyl)-vinyl]-oxazol-4-ylmethoxy}-benzyloxy)-ethyl]-1H-[1,2,3]triazolium methanesulfonate;

1-[2-(4-{2-[2-(E)-(4-Trifluoromethoxy-phenyl)-vinyl]-oxazol-4-ylmethoxy}-benzyloxy)-ethyl]-1H-[1,2,3]triazolium p-toluenesulfonate; and 1-[2-(4-{2-[2-(E)-(4-Trifluoromethoxy-phenyl)-vinyl]-oxazol-4-ylmethoxy}-benzyloxy)-ethyl]-1H-[1,2,3]triazolium chloride.

A preferred embodiment of the present invention is the compound:

1-[2-(4-{2-[2-(E)-(4-Trifluoromethoxy-phenyl)-vinyl]-oxazol-4-ylmethoxy}-benzyloxy)-ethyl]-1H-[1,2,3]triazole.

Another preferred embodiment of the present invention is the compound:

1-[2-(4-{2-[2-(E)-(4-Difluoromethoxy-phenyl)-vinyl]-oxazol-4-ylmethoxy}-benzyloxy)-ethyl]-1H-[1,2,3]triazole.

Yet another embodiment of the present invention are the compounds of formula I, wherein:

$R^1$ is —O—$CF_3$; —O—$CHF_2$ or —S—$CF_3$;
$R^2$ is halogen; and
$R^3$ and $R^4$ are hydrogen; and pharmaceutically acceptable salts or esters thereof.

Such compounds are for example:

1-[2-(4-{2-[2-(E)-(2-Fluoro-4-trifluoromethoxy-phenyl)-vinyl]-oxazol-4-ylmethoxy}-benzyloxy)-ethyl]-1H-[1,2,3]triazole; and 1-[2-(4-{2-[2-(E)-(2-Fluoro-4-trifluoromethylsulfanyl-phenyl)-vinyl]-oxazol-4-ylmethoxy}-benzyloxy)-ethyl]-1H-[1,2,3]triazole.

Yet another embodiment of the invention are the compounds of formula I, wherein:

$R^1$ and $R^2$ together with the carbon atoms to which they are attached form 2,2-Difluoro-benzo[1,3]dioxolyl;
$R^3$ and $R^4$ are hydrogen; and pharmaceutically acceptable salts or esters thereof.

Such a compound is for example:

1-[2-(4-{2-[2-(E)-(2,2-Difluoro-benzo[1,3]dioxol-5-yl)-vinyl]-oxazol-4-ylmethoxy}-benzyloxy)-ethyl]-1H-[1,2,3]triazole.

Yet another embodiment of the present invention are the compounds of formula I, wherein:

$R^1$ and $R^2$ together with the carbon atoms to which they are attached form 2,2-Difluoro-benzo[1,3]dioxolyl;
$R^3$ is halogen;
$R^4$ is hydrogen; and pharmaceutically acceptable salts or esters thereof.

Such a compound is for example:

1-[2-(4-{2-[2-(E)-(2,2,6-Trifluoro-benzo[1,3]dioxol-5-yl)-vinyl]-oxazol-4-ylmethoxy}-benzyloxy)-ethyl]-1H-[1,2,3]triazole.

Yet another embodiment of the invention is a compound of formula I-A,

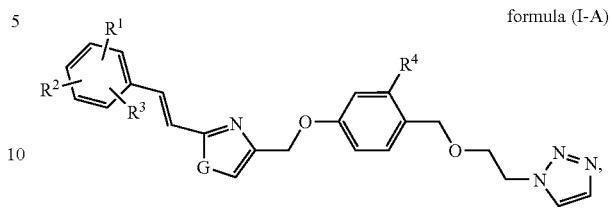

formula (I-A)

wherein:
G is oxygen or sulfur;
$R^4$ is fluorine, methyl, or methoxy;
and, either:
(A) $R^1$ is selected from the group consisting of:
  (a) —O-alkyl, wherein the alkyl group is optionally substituted with one or more halogen atoms;
  (b) —S-alkyl, wherein the alkyl group is optionally substituted with one or more halogen atoms;
  (c) —NH-alkyl, wherein the alkyl group is optionally substituted with one or more halogen atoms;
$R^2$ is hydrogen or halogen; and
$R^3$ is hydrogen;
or, alternatively,
(B)
$R^1$ and $R^2$, together with the carbon atoms to which they are attached, form a 5 or 6 membered heterocyclic ring, optionally substituted with one or more halogen atoms, and $R^3$ is hydrogen or halogen;
or a pharmaceutically acceptable salt or ester thereof.

Such compounds are for example:

1-[2-(2-Fluoro-4-{2-[2-(E)-(4-difluoromethoxy-phenyl)-vinyl]-oxazol-4-ylmethoxy}-benzyloxy)-ethyl]-1H-[1,2,3]-triazole;

1-[2-(2-Methyl-4-{2-[2-(E)-(4-difluoromethoxy-phenyl)-vinyl]-oxazol-4-ylmethoxy}-benzyloxy)-ethyl]-1H-[1,2,3]-triazole;

1-[2-(2-Methoxy-4-{2-[2-(E)-(4-difluoromethoxy-phenyl)-vinyl]-oxazol-4-ylmethoxy}-benzyloxy)-ethyl]-1H-[1,2,3]-triazole;

1-[2-(2-Fluoro-4-{2-[2-(E)-(4-trifluoromethoxy-phenyl)-vinyl]-oxazol-4-ylmethoxy}-benzyloxy)-ethyl]-1H-[1,2,3]-triazole;

1-[2-(2-Methyl-4-{2-[2-(E)-(4-trifluoromethoxy-phenyl)-vinyl]-oxazol-4-ylmethoxy}-benzyloxy)-ethyl]-1H-[1,2,3]-triazole;

1-[2-(2-Methoxy-4-{2-[2-(E)-(4-trifluoromethoxy-phenyl)-vinyl]-oxazol-4-ylmethoxy}-benzyloxy)-ethyl]-1H-[1,2,3]-triazole;

1-[2-(2-Fluoro-4-{2-[2-(E)-(4-trifluoromethylsulfanyl-phenyl)-vinyl]-oxazol-4-ylmethoxy}-benzyloxy)-ethyl]-1H-[1,2,3]-triazole;

1-[2-(2-Methyl-4-{2-[2-(E)-(4-trifluoromethylsulfanyl-phenyl)-vinyl]-oxazol-4-ylmethoxy}-benzyloxy)-ethyl]-1H-[1,2,3]-triazole; and 1-[2-(2-Methoxy-4-{2-[2-(E)-(4-trifluoromethylsulfanyl-phenyl)-vinyl]-oxazol-4-ylmethoxy}-benzyloxy)-ethyl]-1H-[1,2,3]-triazole.

Another embodiment of the invention is a compound according to formula I-A, wherein:

G is oxygen;
$R^3$ is hydrogen;
$R^4$ is hydrogen, $C_1$-$C_3$ alkyl, or fluorine;

and, either:
(A) $R^1$ is selected from the group consisting of:
   (a) —O-alkyl; wherein the alkyl group is optionally substituted with one or more fluorine atoms; and
   (b) —S-alkyl; wherein the alkyl group is optionally substituted with one or more fluorine atoms; and
$R^2$ is hydrogen;
or, alternatively,
(B) $R^1$ and $R^2$, together with the carbon atoms to which they are attached, form 2,2-Difluoro-benzo[1,3]dioxolyl;
or a pharmaceutically acceptable salt or ester salts or esters thereof.

Yet another embodiment of the invention are the compounds of formula I-B

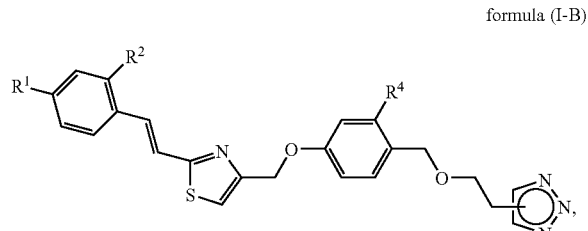

formula (I-B)

wherein:
$R^1$ is —O—CF$_3$ or —O—CHF$_2$;
$R^2$ is hydrogen or halogen;
$R^4$ is hydrogen, methyl, methoxy, or fluorine; and their pharmaceutically acceptable salts or esters.
Such compounds are for example:
1-[2-(4-{2-[2-(E)-(4-trifluoromethoxy-phenyl)-vinyl]-thiazol-4-ylmethoxy}-benzyloxy)-ethyl]-1H-[1,2,3]triazole;
1-[2-(4-{2-[2-(E)-(4-difluoromethoxy-phenyl)-vinyl]-thiazol-4-ylmethoxy}-benzyloxy)-ethyl]-1H-[1,2,3]-triazole;
1-[2-(2-Fluoro-4-{2-[2-(E)-(4-difluoromethoxy-phenyl)-vinyl]-thiazol-4-ylmethoxy}-benzyloxy)-ethyl]-1H-[1,2,3]-triazole;
1-[2-(2-Methyl-4-{2-[2-(E)-(4-difluoromethoxy-phenyl)-vinyl]-thiazol-4-ylmethoxy}-benzyloxy)-ethyl]-1H-[1,2,3]-triazole;
1-[2-(2-Methoxy-4-{2-[2-(E)-(4-difluoromethoxy-phenyl)-vinyl]-thiazol-4-ylmethoxy}-benzyloxy)-ethyl]-1H-[1,2,3]triazole;
1-[2-(2-Fluoro-4-{2-[2-(E)-(4-trifluoromethoxy-phenyl)-vinyl]-thiazol-4-ylmethoxy}-benzyloxy)-ethyl]-1H-[1,2,3]triazole;
1-[2-(2-Methyl-4-{2-[2-(E)-(4-trifluoromethoxy-phenyl)-vinyl]-thiazol-4-ylmethoxy}-benzyloxy)-ethyl]-1H-[1,2,3]triazole;
1-[2-(2-Methoxy-4-{2-[2-(E)-(4-trifluoromethoxy-phenyl)-vinyl]-thiazol-4-ylmethoxy}-benzyloxy)-ethyl]-1H-[1,2,3]-triazole; and
4-[2-(4-{2-[2-(E)-(4-trifluoromethoxy-phenyl)-vinyl]-thiazol-4-ylmethoxy}-benzyloxy)-ethyl]-1H-[1,2,3]-triazole.

Still another embodiment are the pharmaceutically acceptable salts of the compounds of formula I-B such as:
1-[2-(4-{2-[2-(E)-(4-trifluoromethoxy-phenyl)-vinyl]-thiazol-4-ylmethoxy}-benzyloxy)-ethyl]-1H-[1,2,3]triazolium methanesulfonate;
1-[2-(4-{2-[2-(E)-(4-trifluoromethoxy-phenyl)-vinyl]-thiazol-4-ylmethoxy}-benzyloxy)-ethyl]-1H-[1,2,3]triazolium p-toluenesulfonate; or
1-[2-(4-{2-[2-(E)-(4-trifluoromethoxy-phenyl)-vinyl]-thiazol-4-ylmethoxy}-benzyloxy)-ethyl]-1H-[1,2,3]triazolium chloride.

Still another embodiment of the invention is a process for the manufacture of the compounds of formula (I), wherein:
(a) the compound of formula (V)

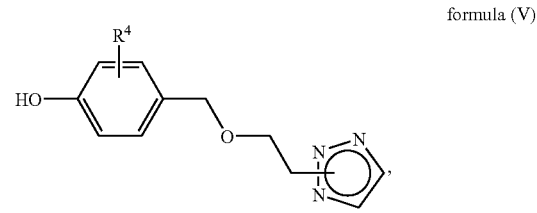

formula (V)

wherein $R^4$ has the significance given in formula (I), is reacted with a compound of formula (IV)

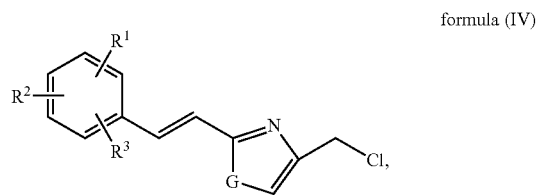

formula (IV)

wherein $R^1$, $R^2$, $R^3$ and G have the significance given in formula (I), to give the respective compound of formula (I);
(b) said compound of formula (I) is isolated from the reaction mixture, and
(c) if desired, converted into a pharmaceutically acceptable salt.

The ether derivatives of the general formula (I), or a pharmaceutically acceptable salt thereof, may be prepared by any process known to be applicable for the preparation of chemically-related compounds by the one skilled in the art. Such processes, when used to prepare the ether derivatives of formula (I), or a pharmaceutically-acceptable salt thereof, are provided as a further feature of the invention and are illustrated by the following representative examples of scheme 1, in which, unless otherwise stated, $R^1$, $R^2$, $R^3$, $R^4$ and G have the significance given herein before with respect to formula (I). Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

Scheme 1

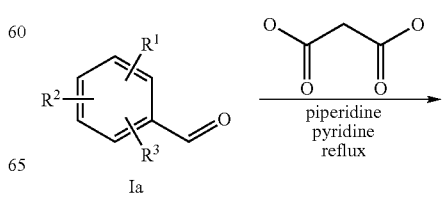

Ia

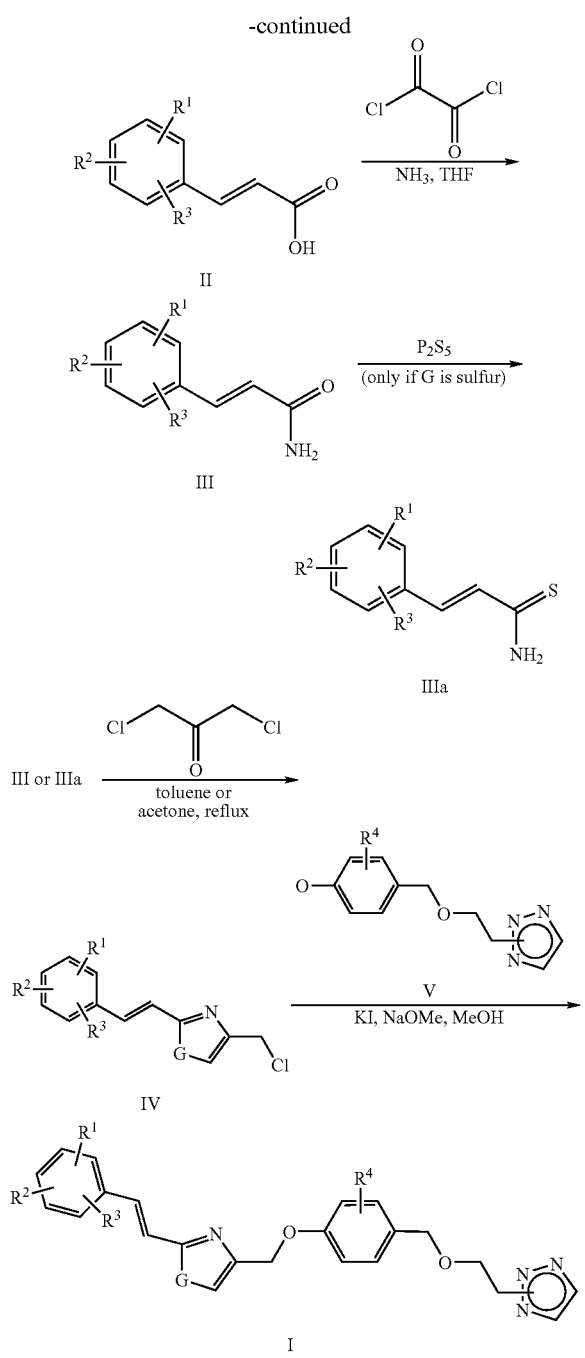

A preferred method for the synthesis of the compounds of the present invention is described in scheme 1, and starts from the corresponding benzaldehydes (Ia). The first step of the reaction sequence is a condensation with malonic acid and concomitant decarboxylation, yielding acrylic acids of formula (II). The reaction is typically carried out in solvents like pyridine, N-methylpyrrolidinone, acetonitrile, N,N-dimethylformamide and mixtures thereof at temperatures up to 140° C. Typically used bases are piperidine, triethylamine and diisopropylamine.

The obtained acrylic acids of formula (II) are converted into their corresponding amides of formula (III) by standard methods for someone skilled in the art, e.g. by activating the carboxylic group in (II) with oxalyl chloride in solvents like tetrahydrofuran, dichloromethane, N,N-dimethylformamide and mixtures thereof at temperatures varying from −30° C. to 40° C. The addition of ammonia yields said amides of formula (III).

In order to obtain the compounds of formula (I) wherein "G" is sulfur, the carboxamides of formula (III) need to be converted into the corresponding thioamides of formula (IIIa), e.g. by reaction with phosphorous pentasulfide in a solvent like THF or dioxane, preferably at reflux temperature. On the other hand, in order to obtain the compounds of formula (I) wherein "G" is oxygen, this reaction step is avoided and the compounds of formula (III) are immediately reacted with 1,3-dichloro-propan-2-one to give the corresponding chlorides of formula (IV). Chlorides of formula (IV) can be synthesized by a commonly known method or a modification thereof. Amides of formula (III) or (IIIa) and 1,3-dichloroacetone are subjected to a condensation/dehydration sequence yielding the compounds of formula (IV). Typical solvents for reactions of this kind are toluene, xylene, benzene, acetone and chloroform. If desired, the reaction can be carried out under solvent free conditions. The reaction temperatures may vary from 50° C. to 150° C., the thioamides of formula (IIIa) being more reactive than the amides of formula (III).

The ether derivatives of formula (I) can be obtained by reactions well known to someone skilled in the art, e.g. by alkylation of compounds of formula (V) with compounds of formula (IV) according to scheme 1. Typically the alkylation is carried out in the presence of potassium iodide or sodium iodide in solvents like methanol, ethanol and isopropanol. Typical bases for this reaction are sodium methylate, sodium hydride or lithium diisopropyl amide. The reaction temperatures may vary from 50° C. to 150° C.

The phenolic compounds of formula (V) may be prepared by: (a) reaction of a compound of formula (VI) with a compound of formula (VII)

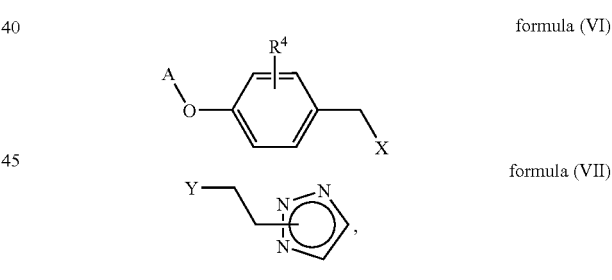

formula (VI)

formula (VII)

wherein "A" denotes a suitable protecting group as defined below, $R^4$ has the meaning given in formula (I), and one of X and Y denotes a hydroxy group while the other denotes a suitable leaving group E as defined below, and (b) subsequent removal of the protecting group A.

Reactions of compounds of formula (VI) with compounds of formula (VII) are well known in the art. Typically, such alkylation reaction may be carried out in solvents like N,N-dimethylformamide, methanol, ethanol and isopropanol. Typical bases for this reaction are alkaline carbonates, sodium methylate, sodium hydride or lithium diisopropyl amide. The reaction temperatures may vary from 20° C. to 150° C. Other preferred alkylation procedures make use of alkaline carbonates as bases in solvents like ketones, for example cesium carbonate in butanone at reflux temperature, or sodium hydride in DMF at room temperature. Suitable leaving groups "E" are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoromethansulfonate (triflate) or the azido group.

A protecting group "A" as mentioned herein is preferably, but not limited to tert-butoxycarbonyl (boc), propen-3-yl (allyl), triphenylmethyl (trityl) and silyl groups, e.g. tert.-butyldimethyl-silyl, triisopropyl-silyl.

Removal of a protecting group on a hetero atom depends on the nature of such group. Typical examples are the removal of a trityl group under acidic conditions, for example with aqueous formic acid in THF under reflux or the removal of a tert-butoxycarbonyl group with trifluoroacetic acid in dichloromethane at room temperature or the removal of a substituted silyl group with tetrabutylammonium fluoride in aqueous THF at room temperature. An allyl group can smoothly be removed by treating the substrate with catalytic amounts of a palladium complex, e.g. $Pd(PPh_3)_4$ in dichloromethane in presence of an allyl-acceptor such as 1,3-dimethylbarbituric acid.

The compounds of formula (I) can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds of formula (I) and their pharmaceutically acceptable salts or esters possess valuable pharmacological properties. It has been found that said compounds inhibit the HER-signaling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signaling pathway inhibitors is demonstrated by the following biological assay:

Inhibition of HER2 Phosphorylation in Calu3 Tumor Cell Line $2 \times 10^5$ Calu3 cells [Calu-3 (HTB-55) cells available from ATTC] per well were plated 12-well plate. After 4 days cells were starved for 16 h in DMEM/0.5% FCS/1% Glutamine. During this time cells were incubated with 1 µM of the compound. Afterwards cells were lysed in lyses buffer containing 1% Triton, 10% Glycerol, 1 mM EGTA, 1.5 mM $MgCl_2$, 150 mM NaCl, 50 mM Hepes pH 7.5, 1 mM PMSF, 10 µg/mL Aprotinin and 0.4 mm Orthovanadate. Cell lysates were analyzed on a SDS PAGE and after transfer to a nitrocellulose membrane detected with an antibody specifically recognizing the pY 1248 in HER2. Inhibition of HER2 phosphorylation is calculated as percentage of the DMSO treated control. This percentage was calculated according to the following formula: Inhibition in %=100−(Phosphorylated-HER2-Signal of Test Sample*100/Phosphorylated-HER2-Signal DMSO-control).

With all compounds a significant inhibition of HER2-phosphorylation was detected, which is exemplified by the compounds shown in Table 1. The reference compounds as used herein are:

Reference compound 1: 1-[4-(4-{2-[2-(4-Trifluoromethyl-phenyl)-vinyl]-oxazol-4-ylmethoxy}-phenyl)-butyl]-1H-[1,2,3]triazole (Example 4, p. 88, WO 01/77107).

Reference compound 2: 1-[2-(4-{2-[(E)-2-(4-Trifluoromethyl-phenyl)-vinyl]-oxazol-4-ylmethoxy}-benzyloxy)-ethyl]-1H-[1,2,3]triazole (Example 2, p. 101, WO 03/059907).

TABLE 1

|  | Control (DMSO) | Percent inhibition of HER2-phosphorylation (compound concentration 1 µM) |
|---|---|---|
| reference compound 1 | 0 | 52.3 |
| reference compound 2 | 0 | 54.0 |
| example 1 | 0 | 69.6 |
| example 2 | 0 | 85.8 |
| example 3 | 0 | 73.4 |
| example 4 | 0 | 78.6 |

In vivo Assay on Tumor Inhibition:

To generate primary tumors, NSCLC (e.g. QG56, A549, Calu-3) cells ($4\text{-}5.0 \times 10^6$ in a volume of 100 µl) are injected subcutaneously into the left flank of female SCID beige mice [severe combined immunodeficient beige mice available from Charles River, Sulzfeld, Deutschland] or BALB/c nude mice [BALB/c nude spontaneous mutant mice (homozygotes) available from Taconic Europe (former Mollegaard and Bomholtgard Breeding and Research Centre in Denmark)] using a 1 ml syringe and a 26G needle. The tumor cells are originally obtained from the NCI and deposited in a working cell bank. The cells are thawed and expanded in vitro before use in the experiment. Mice are assigned to the treatment groups 14-21 days after cell injection. For grouping (n=10-15 mice per group), the animals are randomized to get a similar mean primary tumor volume of ca. 100-150 $mm^3$ per group. The test compounds are administered orally once per day as a suspension in 7.5% gelatine 0.22% NaCl with an administration volume of 10 ml/kg based on actual body weights. Treatment is initiated one day after staging, and carried out until day 20-50, the final day of the study. The subcutaneous primary tumors are measured twice weekly, starting prior to randomisation, in two dimensions (length and width) using an electronic caliper. The volume of the primary tumor is calculated using the formula: $V[mm^3]$=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts or esters can be used as compositions, e.g. in the form of pharmaceutical composition. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. As used herein, a "pharmaceutically acceptable carrier" is intended to include any and all material compatible with pharmaceutical administration. The use of such carriers for pharmaceutically active substances is known in the art. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances. Except insofar as any conventional material is incompatible with the active compound, use thereof in the compositions is contemplated. Supplementary active compounds can also be incorporated into the compositions.

Preferred pharmaceutical compositions comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 (a pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes(here 1 ml steps) until final volume is reached or extract is clear.
10. Fill up to final volume with gelatin and homogenize.

The above described preparation yields micro-suspensions of the compounds of formula I-A with particle sizes between 1 and 10 µm. The suspensions are suitable for oral applications and can be used in the in vivo assay described above.

Compositions containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts or esters and, if desired, one or more other therapeutically valuable substances into a galenical administration form together with one or more therapeutically inert carriers. The dosage depends on various factors such as manner of administration, species, age and/or individual state of health.

The compounds of the present invention as well as their pharmaceutically acceptable salts or esters are useful in the control or prevention of illnesses. For example, the compounds of the present invention are useful for preventing or treating proliferative diseases and conditions such as tumor growth and/or cancer including, but not limited to, breast cancer, leukemia, ovarian cancer, bronchial or lung cancer, pancreatic cancer, and gastrointestinal cancer such as colon cancer, rectal cancer, and stomach cancer. Based on their HER-signaling pathway inhibition and their antiproliferative activity, said compounds are particularly useful for the treatment of diseases such as cancer in humans or animals and for the production of corresponding pharmaceutical compositions.

The compounds of the present invention show activity as inhibitors of the HER-signaling pathway and therefore possess anti-proliferative activity. The present invention provides the compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

The following examples and references are provided to aid the understanding of the present invention, the true scope of which is set forth in the appended claims. It is understood that modifications can be made in the procedures set forth without departing from the spirit of the invention.

EXAMPLES

Example 1

1-[2-(4-{2-[2-(E)-(4-Difluoromethoxy-phenyl)-vinyl]-oxazol-4-ylmethoxy}-benzyloxy)-ethyl]-1H-[1,2,3]triazole i) 1-Allyloxy-4-chloromethyl-benzene 7.67 g (67.0 mmol) methanesulfonyl chloride were given at 0° C. to a solution of 10.0 g (60.9 mmol) (4-allyloxy-phenyl)-methanol and 9.34 ml (67.0 mmol) triethylamine in 35 ml dichloromethane and stirred at r.t. overnight. The mixture was poured in ice water, extracted with dichloromethane and the organic phase dried over $Na_2SO_4$. After removal of solvents the residue was purified by chromatography on silica gel (ethyl acetate/n-heptane 1:5) to yield 3.12 g (28%) pale yellow oil.

$^1$H-NMR(400 MHz, $D_6$-DMSO): δ=4.57(m, 2H, $OCH_2$), 4.72(s, 2H, $CH_2Cl$), 5.26(d, 1H, =$CH_2$), 5.39(d, 1H, =$CH_2$), 6.04(m, 1H, C$\underline{H}$=$CH_2$), 6.95(d, 2H, 2'-/6'-H), 7.35 (d, 2H, 3'-/5'-H).

ii) 1-[2-(4-Allyloxy-benzyloxy)-ethyl]-1H-[1,2,3]triazole 197 mg 8.21 mmol) 95% Sodium hydride were given at −50° C. to a solution of 1.00 g (5.47 mmol) 1-allyloxy-4-chloromethyl-benzene and 619 mg (5.47 mmol) 2-(1H-[1,2,3]-triazol-1-yl)-ethanol in 9.0 ml DMF. The mixture was allowed to warm slowly to r.t., stirred overnight and 10 ml water added. The formed oil was collected with 10 ml dichloromethane, the aqueous phase extracted with 10 ml dichloromethane and the combined organic phases dried over $Na_2SO_4$.

Solvents were removed in vacuum and the residue purified by chromatography on silica gel (ethyl acetate/heptane 1:1) to yield 1.10 g (78%) yellow oil.

MS: M=260.3 (AP+), 258.3 (AP−).

$^1$H-NMR(400 MHz, $D_6$-DMSO): δ=3.79(t, 2H, C$\underline{H}_2$—$CH_2$-triazole), 4.39(s, 2H, $OCH_2Ph$), 4.54-4.59(m, 4H, $OCH_2$-vinyl, $CH_2$-triazole), 5.25(d, 1H, =$CH_2$), 5.38(d, 1H, =$CH_2$), 6.06(m, 1H, C$\underline{H}$=$CH_2$), 6.89(d, 2H, 2'-/6'-H), 7.15 (d, 2H, 3'-/5'-H), 7.16(s, 1H, triazole), 8.08(s, 1H, triazole).

iii) 4-(2-[1,2,3]Triazol-1-yl-ethoxymethyl)-phenol

A solution of 500 mg (1.93 mmol) 1-[2-(4-allyloxy-benzyloxy)-ethyl]-1H-[1,2,3]-triazole in 10 ml dichloromethane was added to a solution of 904 mg (5.79 mmol) 1,3-dimethylbarbituric acid and 58 mg (0.05 mmol) $Pd(PPh_3)_4$ in 20 ml dichloromethane and stirred for 4.5 h at 40° C. The mixture was extracted with 3×20 ml sat. $NaHCO_3$-solution and 8 ml water and the combined aqueous phases were reextracted with 2×10 ml dichloromethane. The organic extracts were combined and dried over $MgSO_4$. Solvents were distilled off and the residue purified by chromatography on silica gel (ethyl acetate) to yield 248 mg (59%) of the title compound.

$^1$H-NMR(400 MHz, $D_6$-DMSO): δ=3.77(t, 2H, C$\underline{H}_2$—$CH_2$-triazole), 4.33(s, 2H, $OCH_2Ph$), 4.56(t, 2H, $CH_2$-triazole), 6.69(d, 2H, 2'-/6'-H), 7.03(d, 2H, 3'-/5'-H), 7.11(s, 1H, triazole), 8.07(s, 1H, triazole), 9.37(s, 1H, PhOH).

iv) 3-(4-Difluoromethoxy-phenyl)-acrylic acid

A mixture of 10.0 g (7.68 ml, 58.1 mmol) 4-difluoromethoxy-benzaldehyde, 6.65 g (63.9 mmol) malonic acid, 0.21 g (2.50 mmol) piperidine and 50 ml pyridine was kept at reflux temperature until carbon dioxide development ceased (3 h). After cooling to room temperature the reaction mixture was poured onto 200 g ice and 100 ml 6N HCl. The precipitate was isolated, washed with water and dried. Yield: 8.8 g (71%) 3-(4-Difluoromethoxy-phenyl)-acrylic acid.

$^1$H-NMR(400 MHz, $D_6$-DMSO): δ=6.51(d, 1H, 2-H), 7.21 (d, 2H, 3'-/5'-H), 7.32(t, 1H, $OCHF_2$), 7.59(d, 1H, 3-H), 7.77 (d, 2H, 2'-/6'-H), 12.4(br, 1H, COOH)

v) 3-(4-Difluoromethoxy-phenyl)-acrylamide

To a suspension of 8.70 g (40.6 mmol) 3-(4-difluoromethoxy-phenyl)-acrylic acid in 60.0 ml tetrahydrofuran and 0.6 ml N,N-dimethylformamide a solution of 5.14 ml (60.9 mmol) oxalyl chloride in 10 ml tetrahydrofuran was added dropwise at 0° C. within 10 min. Stirring was continued at 0-5° C. for 30 min. and 2 h at room temperature thereafter. The resulting solution was cooled to 0-5° C. again and then added within 15 min. to 150 ml of a 25% aqueous ammonia solution. The separating oil was collected and stirred for 30 min. with water. The precipitated amide was collected, washed with water and dried at 40° C. in vacuo. 4.7 g (54%) 3-(4-Difluoromethoxy-phenyl)-acrylamide.

MS: M=214.2 (API+).

$^1$H-NMR(400 MHz, $D_6$-DMSO): δ=6.57(d, 1H, 2-H), 7.10 (br, 1H, NH), 7.21(d, 2H, 3'-/5'-H), 7.29(t, 1H, $CHF_2$), 7.45(d, 1H, 3-H), 7.53(br, 1H, NH), 7.63(d, 2H, 2'-/6'-H).

vi) 4-Chloromethyl-2-[2-(4-difluoromethoxy-phenyl)-vinyl]-oxazole 4.50 g (21.1 mmol) 3-(4-Difluoromethoxy-phenyl)-acrylamide, 3.20 g (25.2 mmol) 1,3-dichloroacetone and 45 ml toluene were kept at reflux temperature for 22 h with continuous removal of water by use of a Dean-Stark trap. After removal of solvents in vacuo, the residue was stirred with diethyl ether, the precipitation (some remaining starting material) sucked off and the filtrate evaporated to dryness. The residue was extracted three times with heptane, the heptane fractions evaporated and the residue dried in vacuo. 1.0 g (16%) 4-Chloromethyl-2-[2-(4-difluoromethoxy-phenyl)-vinyl]-oxazole.

MS: M=286.2(API+)

$^1$H-NMR(400 MHz, $D_6$-DMSO): δ=4.70(s, 2H, $CH_2Cl$, 7.14(d, 1H, =CH), 7.22(d, 2H, Ar—H), 7.31(t, 1H, $OCHF_2$), 7.54(d, 1H, =CH), 7.80(d, 2H, Ar—H), 8.17(s, 1H, oxazole).

vii) 1-[2-(4-{2-[2-(E)-(4-Difluoromethoxy-phenyl)-vinyl]-oxazol-4-ylmethoxy}-benzyloxy)-ethyl]-1H-[1,2,3]triazole 23 mg (0.91 mmol) 95% Sodium hydride were given to a solution of 200 mg (0.91 mmol) 4-(2-[1,2,3]triazol-1-yl-ethoxymethyl)-phenol in 5.0 ml DMF and stirred for 15 min. 260 mg (0.91 mmol) 4-chloromethyl-2-[2-(4-difluoromethoxy-phenyl)-vinyl]-oxazole were added and stirring continued at r.t. for 12 h. After addition of 20 ml water the resulting precipitate was collected, washed with water (2×10 ml), methanol/water 1:1 (2×10 ml), a small amount of diethyl ether and dried in vacuo at 40° C. to yield 256 mg (60%) of the product as beige powder.

¹H-NMR(400 MHz, D$_6$-DMSO): δ=3.80(t, 2H, CH$_2$—CH$_2$-triazole), 4.40(s, 2H, OCH$_2$-Ph) 4.58(t, 2H, CH$_2$-triazole), 5.00(s, 2H, OCH$_2$-oxazole), 6.99(d, 2H, Ar—H), 7.09-7.25(m, 5H, Ar—H, vinyl-H) 7.14(d, 16.7 Hz, 1H, vinyl-H), 7.30 (t, 74.0 Hz, 1H, OCF$_2$H), 7.53(d, 16.7 Hz, 1H, vinyl-H), 7.72(s, 1H, triazole), 7.79 (d, 2H, Ar—OCHF$_2$), 8.16(s, 1H, triazole), 8.20(s, 1H, oxazole).

Example 2

1-[2-(4-{2-[2-(E)-(2,2-Difluoro-benzo[1,3]dioxol-5-yl)-vinyl]-oxazol-4-ylmethoxy}-benzyloxy)-ethyl]-1H-[1,2,3]triazole i) 3-(2,2-Difluoro-benzo[1,3]dioxol-5-yl)-acrylic acid A mixture of 10.0 g (53.7 mmol) 2,2-difluoro-benzo[1,3]dioxole-5-carbaldehyde, 6.24 g (60.0 mmol) malonic acid, 0.46 g (5.40 mmol) piperidine and 40 ml pyridine was kept at reflux temperature until carbon dioxide development ceased (3 h). After cooling to room temperature the reaction mixture was poured onto 100 g ice and 30 ml 6N HCl. The precipitate was isolated, washed with water and dried. Yield: 8.60 g (70%) 3-(2,2-Difluoro-benzo[1,3]dioxol-5-yl)-acrylic acid.

ii) 3-(2,2-Difluoro-benzo[1,3]dioxol-5-yl)-acrylamide

To a suspension of 8.00 g (35.1 mmol) 3-(2,2-difluoro-benzo[1,3]dioxol-5-yl)-acrylic acid in 40 ml tetrahydrofuran and 0.4 ml N,N-dimethyl formamide, 3.86 ml (45.0 mmol) oxalyl chloride was added dropwise at 0° C. within 10 min. Stirring was continued at 0-5° C. for 30 min. and 2 h at room temperature thereafter. The resulting solution was cooled to 0-5° C. again and then added within 15 min. to 34 ml of an 25% aqueous solution of ammonia. After stirring for 30 min. the precipitated amide was collected, washed with water and dried at 40° C. in vacuo. 7.20 g (90%) 3-(2,2-Difluoro-benzo[1,3]dioxol-5-yl)-acrylamide were obtained.

¹H-NMR(400 MHz, D$_6$-DMSO): δ=6.59(d, 1H, 2-H), 7.14 (br, 1H, NH), 7.41-7.46(m, 3H, 3-H/7'-H/6'-H), 7.53(br, 1H, NH), 7.66(s, 1H, 4'-H).

iii) 4-Chloromethyl-2-[2-(2,2-difluoro-benzo[1,3]dioxol-5-yl)-vinyl]-oxazole 6.90 g (30.4 mmol) 3-(2,2-Difluoro-benzo[1,3]dioxol-5-yl)-acrylamide, 4.76 g (37.5 mmol) 1,3-dichloroacetone and 50 ml toluene were kept at reflux temperature for 48 h with continuous removal of water by applying a Dean-Stark trap. After removal of solvents in vacuo, the residue was treated with 60 ml of a 1:1 mixture of water/isopropanol. After filtration the precipitate was washed first with isopropanol, then with heptane. Drying at 40° C. in vacuo gave 4-Chloromethyl-2-[2-(2,2-difluoro-benzo[1,3]dioxol-5-yl)-vinyl]-oxazole.

MS: M=300.0 (API+).

¹H-NMR(400 MHz, D$_6$-DMSO): δ=4.70(s, 2H, CH$_2$Cl), 7.20(d, 1H, 2-H), 7.45(d, 1H, 7'-H), 7.55(d, 1H, 3-H),), 7.56 (d, 1H, 6'-H), 7.92(s, 1H, 4'-H), 8.18(s, 1H, oxazole).

iv) 1-[2-(4-{2-[2-(E)-(2,2-Difluoro-benzo[1,3]dioxol-5-yl)-vinyl]-oxazol-4-ylmethoxy}-benzyloxy)-ethyl]-1H-[1,2,3]triazole 25 mg (1.00 mmol) 95% Sodium hydride were given to a solution of 219 mg (1.00 mmol) 4-(3-[1,2,3]triazol-1-yl-propoxy)-phenol in 5.0 ml DMF and stirred for 15 min. 300 mg (1.00 mmol) 4-chloromethyl-2-[2-(2,2-difluoro-benzo[1,3]dioxol-5-yl)-vinyl]-oxazole were added and stirring continued at r.t. for 12 h. After addition of 20 ml water the resulting precipitate was collected, washed with water (2×10 ml), methanol/water 1:1 (2×10 ml), and a small amount of diethyl ether and dried in vacuo at 40° C. to yield 351 mg (73%) of a beige powder.

¹H-NMR(400 MHz, D$_6$-DMSO): δ=3.82(t, 2H, CH$_2$—CH$_2$-triazole), 4.41(s, 2H, OCH$_2$-Ph), 4.59(t, 2H, CH$_2$-triazole), 5.02(s, 2H, OCH$_2$-oxazole), 7.00(d, 2H, 3'-/5'-H—Ar), 7.18(d, 2H, 2'-/6'-H—Ar) 7.20(d, 1H, vinyl-H), 7.45(d, 1H, ArO$_2$CF$_2$), 7.51-7.60(m, 2H, vinyl-H, ArO$_2$CF$_2$), 7.72(s, 1H, triazole), 7.92(d, 1H, ArO$_2$CF$_2$), 8.08(s, 1H, triazole), 8.20(s, 1H, oxazole).

Example 3

1-[2-(4-{2-[2-(E)-(4-Trifluoromethylsulfanyl-phenyl)-vinyl]-oxazol-4-ylmethoxy}-benzyloxy)-ethyl]-1H-[1,2,3]triazole i) 3-(4-Trifluoromethylsulfanyl-phenyl)-acrylic acid A mixture of 5.42 g (26.3 mmol) 4-trifluoromethylsulfanyl-benzaldehyde, 3.12 g (30.0 mmol) malonic acid, 0.26 g (3.0 mmol) piperidine and 12.0 ml pyridine was kept at reflux temperature until carbon dioxide development ceased (5 h). After cooling to room temperature, the reaction mixture was poured onto 50 g ice and 15 ml 6N HCl. The precipitate was isolated, washed with water and dried. Yield: 5.90 g (90%) 3-(4-Trifluoromethylsulfanyl-phenyl)-acrylic acid.

¹H-NMR(400 MHz, D$_6$-DMSO): δ=6.65(d, 1H, 2-H), 7.63 (d, 1H, 3-H), 7.74(d, 2H, 3'-/5'-H), 7.84(d, 2H, 2'-/6'-H), 12.7(br, 1H, COOH).

ii) 3-(4-Trifluoromethylsulfanyl-phenyl)-acrylamide

To a suspension of 5.24 g (21.1 mmol) 3-(4-trifluoromethylsulfanyl-phenyl)-acrylic acid in 30.0 ml tetrahydrofuran and 0.3 ml N,N-dimethylformamide a solution of 2.70 ml (32.0 mmol) oxalyl chloride in 5.0 ml tetrahydrofuran was added dropwise at 0° C. within 20 min. Stirring was continued at 0-5° C. for 30 min. and 3 h at room temperature thereafter. The resulting solution was cooled to 0-5° C. again and then added within 15 min. to 100 ml of a 25% aqueous ammonia solution. After evaporation of the organic solvent, 200 ml water were added and the solution cooled. The precipitated amide was collected, washed with water and dried at 40° C. in vacuo. Yield 4.62 g (89%) 3-(4-Trifluoromethylsulfanyl-phenyl)-acrylamide.

MS: M=248.2(API+)

¹H-NMR(400 MHz, D$_6$-DMSO): δ=6.72(d, 1H, 2-H), 7.21 (br, 1H, NH), 7.46(d, 1H, 3-H), 7.62(br, 1H, NH), 7.73(dd, 4H, Ar—H).

iii) 4-Chloromethyl-2-[2-(4-trifluoromethylsulfanyl-phenyl)-vinyl]-oxazole 4.45 g (18.0 mmol) 3-(4-Trifluoromethylsulfanyl-phenyl)-acrylamide, 2.80 g (22.2 mmol) 1,3-dichloroacetone and 50.0 ml toluene were kept at reflux temperature for 40 h with continuous removal of water by use of a Dean-Stark trap. After removal of solvents in vacuo, the residue was purified by chromatography on silica gel (eluent: heptane/ethyl acetate 1:1). All fractions containing the product were concentrated to a volume of 10 ml and the crystallized material isolated by filtration, washed with cold heptane and dried.

Yield 2.02 g (35%) 4-Chloromethyl-2-[2-(4-trifluoromethyl-sulfanyl-phenyl)-vinyl]-oxazole.

MS: M=320.1(API+)

$^1$H-NMR(400 MHz, D$_6$-DMSO): δ=4.71(s, 2H, CH$_2$Cl), 7.30(d, 1H, =CH), 7.59(d, 1H, =CH), 7.74(d, 2H, Ar—H), 7.89(d, 2H, Ar—H), 8.21(s, 1H, oxazole).

iv) 1-[2-(4-{2-[2-(E)-(4-Trifluoromethylsulfanyl-phenyl)-vinyl]-oxazol-4-ylmethoxy}-benzyloxy)-ethyl]-1H-[1,2,3]triazole 25 mg (1.00 mmol) 95% Sodium hydride were given to a solution of 219 mg (1.00 mmol) 4-(2-[1,2,3]triazol-1-yl-ethoxymethyl)-phenol in 5.0 ml DMF and stirred for 15 min. 304 mg (1.00 mmol) 4-Chloromethyl-2-[2-(4-trifluoromethylsulfanyl-phenyl)-vinyl]-oxazole were added and stirring continued at r.t. overnight. After addition of 20 ml water the resulting precipitate was washed twice with 10 ml water, 2×10 ml methanol, diethyl ether and dried at 45° C. in vacuum. Yield 301 mg (60%) pale beige powder.

$^1$H-NMR(400 MHz, D$_6$-DMSO): δ=3.80(t, 2H, CH$_2$—CH$_2$-triazole), 4.40(s, 2H, OCH$_2$-Ph), 4.58(t, 2H, CH$_2$-triazole), 5.02(s, 2H, OCH$_2$-oxazole), 6.99(d, 2H, 3'-/5'-H—Ar), 7.18(d, 2H, 2'-/6'-H—Ar) 7.31(d, 1H, vinyl-H), 7.58(d, 1H, vinyl-H), 7.74(d, 2H, ArSCF$_3$), 7.72(s, 1H, triazole), 7.74(d, 2H, ArSCF$_3$), 8.08(s, 1H, triazole), 8.24(s, 1H, oxazole).

Example 4

1-[2-(4-{2-[2-(E)-(4-Trifluoromethoxy-phenyl)-vinyl]-oxazol-4-ylmethoxy}-benzyloxy)-ethyl]-1H-[1,2,3]triazole i) 3-(4-Trifluoromethoxy-phenyl)-acrylic acid A mixture of 5.00 g (3.80 ml, 26.3 mmol) 4-trifluoromethoxy-benzaldehyde, 3.10 g (30.0 mmol) malonic acid, 0.26 g (3.0 mmol) piperidine and 15.0 ml pyridine was kept at reflux temperature until carbon dioxide development ceased (3 h). After cooling to room temperature the reaction mixture was poured onto 50 g ice and 15 ml 6N HCl. The precipitate was isolated, washed with water and dried. Yield: 5.20 g (85%) 3-(4-Trifluoromethoxy-phenyl)-acrylic acid.

$^1$H-NMR(400 MHz, D$_6$-DMSO): δ=6.57(d, 1H, 2-H), 7.40 (d, 2H, 3'-/5'-H), 7.62(d, 1H, 3-H), 7.84(d, 2H, 2'-/6'-H), 12.5(br, 1H, COOH).

ii) 3-(4-Trifluoromethoxy-phenyl)-acrylamide

To a suspension of 4.90 g (21.1 mmol) 3-(4-Trifluoromethoxy-phenyl)-acrylic acid in 30.0 ml tetrahydrofuran and 0.3 ml N,N-dimethyl formamide a solution of 2.70 ml (32.0 mmol) oxalyl chloride in 5.0 ml tetrahydrofuran was added dropwise at 0° C. within 10 min. Stirring was continued at 0-5° C. for 30 min. and 2 h at room temperature thereafter. The resulting solution was cooled to 0-5° C. again and then added within 15 min. to 75 ml of a 25% aqueous ammonia solution. After stirring for 30 min. the precipitated amide was collected, washed with water and dried at 40° C. in vacuo. 4.48 g (92%) 3-(4-Trifluoromethoxy-phenyl)-acrylamide.

MS: M=232.2(API+)

$^1$H-NMR(400 MHz, D$_6$-DMSO): δ=6.63(d, 1H, 2-H), 7.16 (br, 1H, NH), 7.42(d, 2H, 3'-/5'-H), 7.45(d, 1H, 3-H), 7.58(br, 1H, NH), 7.70(d, 2H, 2'-/6'-H).

iii) 4-Chloromethyl-2-[2-(4-trifluoromethoxy-phenyl)-vinyl]-oxazole 4.28 g (18.5 mmol) 3-(4-Trifluoromethoxy-phenyl)-acrylamide, 2.80 g (22.2 mmol) 1,3-dichloroacetone and 30.0 ml toluene were kept at reflux temperature for 16 h with continuous removal of water by use of a Dean-Stark trap. After removal of solvents in vacuo, the residue was purified by chromatography on silica gel (eluent: heptane/ethyl acetate 20:1). All fractions containing the product were concentrated to a volume of 10 ml and the crystallized material isolated by filtration, washed with cold heptane and dried. 1.75 g (31%) 4-Chloromethyl-2-[2-(4-trifluoromethoxy-phenyl)-vinyl]-oxazole.

MS: M=304.2(API+)

$^1$H-NMR(400 MHz. D$_6$-DMSO): δ=4.71(s, 2H, CH$_2$Cl), 7.21(d, 1H, =CH), 7.40(d, 2H, Ar—H), 7.58(d, 1H, =CH), 7.87(d, 2H, Ar—H), 8.19(s, 1H, oxazole).

iv) 1-[2-(4-{2-[2-(E)-(4-Trifluoromethoxy-phenyl)-vinyl]-oxazol-4-ylmethoxy}-benzyloxy)-ethyl]-1H-[1,2,3]triazole 25 mg (1.00 mmol) 95% Sodium hydride were given to a solution of 219 mg (1.00 mmol) 4-(2-[1,2,3]triazol-1-yl-ethoxymethyl)-phenol in 5.0 ml DMF and stirred for 15 min. 304 mg (1.00 mmol) 4-Chloromethyl-2-[2-(4-trifluoromethoxy-phenyl)-vinyl]-oxazole were added and stirring continued at r.t. overnight. After addition of 20 ml water the resulting precipitate was washed twice with 10 ml water, 2×10 ml methanol, diethyl ether and dried at 45° C. in vacuum. Yield 352 mg (72%) colorless powder.

$^1$H-NMR(400 MHz, D$_6$-DMSO): δ=3.80(t, 2H, CH$_2$—CH$_2$-triazole), 4.40(s, 2H, OCH$_2$-Ph), 4.58(t, 2H, CH$_2$-triazole), 5.01(s, 2H, OCH$_2$-oxazole), 6.99(d, 2H, 3'-/5'-H—Ar), 7.18(d, 2H, 2'-/6'-H—Ar) 7.21(d, 1H, vinyl-H), 7.40(d, 2H, ArOCF$_3$), 7.57(d, 1H, vinyl-H), 7.72(s, 1H, triazole), 7.87(d, 2H, ArOCF$_3$), 8.08(s, 1H, triazole), 8.22(s, 1H, oxazole).

Example 5

2-[2-(4-{2-[2-(E)-(4-Trifluoromethoxy-phenyl)-vinyl]-oxazol-4-ylmethoxy}-benzyloxy)-ethyl]-2H-[1,2,3]triazole i) 2-[2-(4-Allyloxy-benzyloxy)-ethyl]2H-[1,2,3]triazole 207 mg (8.21 mmol) 95% Sodium hydride were given at −50° C. to a solution of 1.00 g (5.47 mmol) 1-allyloxy-4-chloromethyl-benzene and 619 mg (5.47 mmol) 2-(2H-[1,2,3]-triazol-2-yl)-ethanol in 10.0 ml DMF. The mixture was allowed to warm slowly to r.t., stirred overnight and 6 ml water added. The formed oil was collected with 10 ml dichloromethane, the aqueous phase extracted with 10 ml dichloromethane and the combined organic phases dried over Na$_2$SO$_4$.

Solvents were removed in vacuum and the residue purified by chromatography on silica gel (ethyl acetate/heptane 1:1) to yield 992 mg (70%) pale yellow oil.

MS: M=282.3 (ESI+, M+Na$^+$).

$^1$H-NMR(400 MHz, D$_6$-DMSO): δ=3.86(t, 2H, CH$_2$—CH$_2$-triazole), 4.35(s, 2H, OCH$_2$Ph), 4.54(d, 2H, OCH$_2$-vinyl), 4.59(t, 2H, CH$_2$-triazole), 5.24(d, 1H, =CH$_2$), 5.37(d, 1H, =CH$_2$), 6.04(m, 1H, CH=CH$_2$), 6.88(d, 2H, 2'-/6'-H), 7.12(d, 2H, 3'-/5'-H), 7.77(s, 2H, triazole).

ii) 4-(2-[1,2,3]Triazol-2-yl-ethoxymethyl)-phenol

A solution of 950 mg (3.66 mmol) 2-[2-(4-allyloxy-benzyloxy)-ethyl]-2H-[1,2,3]-triazole in 20 ml dichloromethane was added to a solution of 1.71 g (11.0 mmol) 1,3-dimethyl-barbituric acid and 104 mg (0.09 mmol) Pd(PPh$_3$)$_4$ in 40 ml dichloromethane and stirred for 4.5 h at 40° C. The mixture was extracted with 3×40 ml sat. NaHCO$_3$-solution and 15 ml water and the combined aqueous phases were reextracted with 2×40 ml dichloromethane. The organic extracts were combined and dried over MgSO$_4$. Solvents were distilled off and the residue purified by chromatography on silica gel (ethyl acetate/n-heptane 2:1) to yield 690 mg (86%) of the title compound.

$^1$H-NMR(400 MHz, D$_6$-DMSO): δ=3.84(t, 2H, CH$_2$—CH$_2$-triazole), 4.29(s, 2H, OCH$_2$Ph), 4.58(t, 2H, CH$_2$-triazole), 6.68(d, 2H, 2'-/6'-H), 7.01(d, 2H, 3'-/5'-H), 7.77(s, 2H, triazole), 9.35(s, 1H, PhOH).

iii) 2-[2-(4-{2-[2-(E)-(4-Trifluoromethoxy-phenyl)-vinyl]-oxazol-4-ylmethoxy}-benzyloxy)-ethyl]-2H-[1,2,3]triazole 25 mg (1.0 mmol) 95% Sodium hydride were given to a solution of 219 mg (1.00 mmol) 4-(2-[1,2,3]triazol-2-yl-ethoxymethyl)-phenol in 5.0 ml DMF and stirred for 15 min. 304 mg (1.00 mmol) 4-Chloromethyl-2-[2-(4-trifluoromethoxy-phenyl)-vinyl]-oxazole were added and stirring continued at r.t. overnight. After addition of 20 ml water the resulting precipitate was washed twice with 10 ml water, 2×10 ml methanol, diethyl ether and dried at 45° C. in vacuum. Yield 254 mg (52%) colorless powder.

$^1$H-NMR(400 MHz, D$_6$-DMSO): δ=3.87(t, 2H, CH$_2$—CH$_2$-triazole), 4.36(s, 2H, OCH$_2$Ph), 4.60(t, 2H, CH$_2$-triazole), 5.00(s, 2H, OCH$_2$-oxazole), 6.97(d, 2H, 3'-/5'-H—Ar), 7.14(d, 2H, 2'-/6'-H—Ar) 7.23(d, 1H, vinyl-H), 7.40(d, 2H, ArOCF$_3$), 7.56(d, 1H, vinyl-H), 7.70-7.86(m, 4H; 2H, triazole; 2H, ArOCF$_3$), 8.22(s, 1H, oxazole).

Example 6

1-[2-(4-{2-[2-(E)-(4-Trifluoromethoxy-phenyl)-vinyl]-thiazol-4-ylmethoxy}-benzyloxy)-ethyl]-1H-[1,2,3]triazole i) 3-(Trifluoromethoxy-phenyl)-thioacrylamide

A mixture of 60.0 g (274 mmol) 3-(4-trifluoromethoxy-phenyl)-acrylamide and 12.2 g (274 mmol) phosphorous pentasulfide in 2.0 l dioxane was stirred under reflux for 4 h. After evaporation, the residue was dissolved at 60° C. in 100 ml isopropanol and 200 ml water added. The precipitate was isolated by filtration, washed with isopropanol/water 1:2 and dried at 40° C. in vacuo to yield 13.0 g (20%) of yellow colored product.

$^1$H-NMR(400 MHz, D$_6$-DMSO): δ=7.01(d, 1H, vinyl-H), 7.41(d, 2H, Ar—H), 7.64(d, 1H, vinyl-H), 7.73(d, 2H, Ar—H), 9.29(s, br, 1H, NH), 9.60(s, br, NH).

ii) 4-Chloromethyl-2-[2-(4-trifluoromethoxy-phenyl)-vinyl]-thiazole 12.7 g (48.3 mmol) 3-(4-Trifluoromethoxy-phenyl)-acrylthioamide, 18.4 g (145 mmol) 1,3-dichloroacetone and 120 ml ethanol were refluxed for 4 h. After evaporation the residue was purified by chromatography on silica gel (ethyl acetate/isohexane 1:10) to yield 2.40 g 4-chloromethyl-2-[2-(4-trifluoromethoxy-phenyl)-vinyl]-thiazole as yellow solid.

$^1$H-NMR(400 MHz, D$_6$-DMSO): δ=4.84(s, 2H, CH$_2$Cl), 7.40(d, 2H, Ar—H), 7.54(s, 2H, vinyl-H), 7.75(s, 1H, thiazole), 7.85(d, 2H, Ar—H).

iii) 1-[2-(4-{2-[2-(E)-(4-Trifluoromethoxy-phenyl)-vinyl]-thiazol-4-ylmethoxy}-benzyloxy)-ethyl]-1H-[1,2,3]triazole 182 mg (7.00 mmol) 95% Sodium hydride were given to a solution of 1.50 g (7.00 mmol) 4-(2-[1,2,3]triazol-1-yl-ethoxymethyl)-phenol in 7.0 ml DMF and stirred for 15 min. 2.06 g (7.00 mmol) 4-Chloromethyl-2-[2-(4-trifluoromethoxy-phenyl)-vinyl]-thiazole were added and stirring continued at r.t. overnight. After addition of 20 ml water the resulting precipitate was washed twice with 10 ml water, then with n-heptane and finally a little amount of diethyl ether and dried at 45° C. in vacuum. Yield 2.4 g.

$^1$H-NMR(400 MHz, D$_6$-DMSO): δ=3.82(t, 2H, CH$_2$—CH$_2$-triazole), 4.41(s, 2H, OCH$_2$-Ph), 4.58(t, 2H, CH$_2$-triazole), 5.18(s, 2H, OCH$_2$-thiazole), 7.00(d, 2H, 3'-/5'-H—Ar), 7.19(d, 2H, 2'-/6'-H—Ar) 7.37(d, 2H, ArOCF$_3$), 7.51(m, 2H, vinyl-H), 7.66, 7.69(2×s, 2×1H, thiazole, triazole), 7.82 (d, 2H, ArOCF$_3$), 8.04(s, 1H, triazole).

Example 7

1-[2-(4-{2-[2-(4-Difluoromethoxy-phenyl)-vinyl]-oxazol-4-ylmethoxy}-2-methyl-benzyloxy)-ethyl]-1H-[1,2,3]triazole i) 4-allyloxy-2-methyl-benzaldehyde 31.7 g (229 mmol) potassium carbonate and 9.51 g (57.3 mmol) potassium iodide were given to a solution of 15.6 g (115 mmol) 4-hydroxy-2-methyl-benzaldehyde and 55.4 g (458 mmol) allyl bromide in 500 ml 2-butanone and stirred for 16 h at 65° C. Solvents were distilled off and the residue distributed between ethyl acetate and 1 N sodium hydroxide. The organic layer was separated and the aqueous solution extracted once with ethyl acetate. The combined organic phases were dried and evaporated to give 19.8 g (98%) of 4-allyloxy-2-methyl-benzaldehyde.

$^1$H-NMR(400 MHz, D$_6$-DMSO): δ=2.59 (s, 3H, CH$_3$), 4.67 (d, 2H, OCH$_2$-vinyl), 5.29 (d, 1H, =CH$_2$), 5.41 (d, 1H, =CH$_2$), 6.05 (m, 1H, CH=CH$_2$), 6.96 (d, 1H, 5-H), 6.74 (s, 1H, 3-H), 7.77 (d, 1H, 6-H), 10.07 (s, 1H, CHO).

ii) (4-allyloxy-2-methyl-phenyl)-methanol 8.50 g (224 mmol) lithium aluminium hydride were given to 250 ml THF and stirred for 20 min. A solution of 19.4 g (110 mmol) 4-allyloxy-2-methyl-benzaldehyde in 100 ml THF was added dropwise and stirring continued for 3 h. The reaction mixture was cooled to 0° C., carefully hydrolysed with 40 ml concentrated ammonium chloride solution, stirred for 60 min. and adjusted to pH=5 with conc. hydrochloric acid. A formed salt precipitate was removed by filtration, washed with THF and the combined organic solutions evaporated. Chromatography of the residue on silica (n-heptane/ethyl acetate 1:3) gave 16.0 g (81%) (4-allyloxy-2-methyl-phenyl)-methanol as a slightly yellow oil.

$^1$H-NMR(400 MHz, D$_6$-DMSO): δ=2.23 (s, 3H, CH$_3$), 4.40 (s, 2H, CH$_2$OH), 4.52 (d, 2H, OCH$_2$-vinyl), 4.88 (t, 1H, OH), 5.23 (d, 1H, =CH$_2$), 5.37 (d, 1H, =CH$_2$), 6.03 (m, 1H, CH=CH$_2$), 6.72 (d, 1H, 5-H), 6.74 (s, 1H, 3-H), 7.20 (d, 1H, 6-H).

iii) 1-allyloxy-4-chloromethyl-2-methyl-benzene

A solution of 16.0 g (89.6 mmol) (4-allyloxy-2-methyl-phenyl)-methanol in 270 ml dichloromethane and 1.5 ml DMF was cooled to 0° C. 7.80 ml (12.8 g, 108 mmol) thionyl chloride were added slowly and then stirred for 1 h at room temperature. Dichloromethane was distilled off, 300 ml toluene added and solvents removed in vacuo. The residue was taken up in 200 ml toluene and washed with concentrated sodium carbonate solution. The organic phase was dried and evaporated to give 17.5 g (99%) 1-allyloxy-4-chloromethyl-2-methyl-benzene as colored oil.

$^1$H-NMR(400 MHz, D$_6$-DMSO): δ=2.34 (s, 3H, CH$_3$), 4.74 (d, 2H, OC$\underline{H}_2$-vinyl), 4.55 (s, 2H, CH$_2$Cl), 5.25 (d, 1H, =CH$_2$), 5.38 (d, 1H, =CH$_2$), 6.02 (m, 1H, C$\underline{H}$=CH$_2$), 6.75 (d, 1H, 5-H), 6.82 (s, 1H, 3-H), 7.29 (d, 1H, 6-H).

iv) 1-[2-(4-Allyloxy-2-methyl-benzyloxy)-ethyl]-1H-[1,2,3]triazole 1.122 g (46.7 mmol) 95% Sodium hydride were given at −50° C. to a solution of 5.630 g (31.2 mmol) 1-allyloxy-4-chloromethyl-2-methyl-benzene and 3.525 g (31.2 mmol) 2-(1H-[1,2,3]-triazol-1-yl)-ethanol in DMF. The mixture was allowed to warm slowly to r. t., stirred for 5 hours. The mixture was concentrated in vacuo and the residue was partitioned between ethyl acetate and water. The organic layer was dried over Na$_2$SO$_4$ and the solvent was distilled off under reduced pressure to yield 7.30 g (86%) 1-[2-(4-Allyloxy-2-methyl-benzyloxy)-ethyl]-1H-[1,2,3]triazole as yellow oil which was used without further purification.

$^1$H-NMR(400 MHz, D$_6$-DMSO): δ=2.10 (s, 3H, CH$_3$), 3.80 (t, 2H, CH$_2$), 4.38 (s, 2H, CH$_2$), 4.52 (d, 2H, OC$\underline{H}_2$-vinyl), 4.57 (t, 2H, CH$_2$), 5.23 (d, 1H, =CH$_2$), 5.37 (d, 1H, =CH$_2$), 6.02 (m, 1H, C$\underline{H}$=CH$_2$), 6.69 (d, 1H, 5-H), 6.74 (s, 1H, 3-H), 7.10 (d, 1H, 6-H), 7.71 (s, 1H), 8.06 (s, 1H).

v) 3-Methyl-4-(2-[1,2,3]triazol-1-yl-ethoxymethyl)-phenol

A solution of 7.30 g (26.7. mmol) 1-[2-(4-Allyloxy-2-methyl-benzyloxy)-ethyl]-1H-[1,2,3]-triazole in 100 ml dichloromethane was added to a solution of 13.02 g (83.4 mmol) 1,3-dimethylbarbituric acid an 959 mg (0.8 mmol) Pd(PPh$_3$)$_4$ in 30 ml dichloromethane and stirred overnight at 40° C. The mixture was extracted with 3× sat. NaHCO$_3$-solution. The combined aqueous phases were extracted with dichloromethane. The combined organic extracts were dried over Na$_2$SO$_4$. Solvents were distilled off and the residue was purified by chromatography on silica gel (heptane/ethyl acetate 1/1 to 0/1) to yield 3.30 g (53%) 3-Methyl-4-(2-[1,2,3]triazol-1-yl-ethoxymethyl)-phenol as a yellow solid melting at 92-93° C.

$^1$H-NMR(400 MHz, D$_6$-DMSO): δ=2.05 (s, 3H, CH$_3$), 3.79 (t, 2H, CH$_2$), 4.33 (s, 2H, CH$_2$), 4.56 (t, 2H, CH$_2$), 6.50 (dd, 1H, 5-H), 6.55 (d, 1H, 3-H), 6.98 (d, 1H, 6-H), 7.70 (s, 1H), 8.05 (s, 1H), 9.25 (s, 1H, OH).

vi) 1-[2-(4-{2-[2-(4-Difluoromethoxy-phenyl)-vinyl]-oxazol-4-ylmethoxy}-2-methyl-benzyloxy)-ethyl]-1H-[1,2,3]triazole A mixture of 201 mg (0.86 mmol) 3-methyl-4-(2-[1,2,3]triazol-1-yl-ethoxymethyl)-phenol and 169 mg (0.52 mmol) cesium carbonate in 10 ml 2-butanone was stirred at 60° C. for 30 minutes, then 246 mg (0.86 mmol) 4-chloromethyl-2-[2-(4-difluoromethoxy-phenyl)-vinyl]-oxazole and 143 mg (0.86 mmol) potassium iodide were added and stirring was continued overnight. After evaporation, the residue was mixed with aqueous NaOH (1N) and extracted with ethyl acetate. The combined extracts were dried, evaporated and the product purified on silica (ethyl acetate) to yield 242 mg (59%) 1-[2-(4-{2-[2-(4-Difluoromethoxy-phenyl)-vinyl]-oxazol-4-ylmethoxy}-2-methyl-benzyloxy)-ethyl]-1H-[1,2,3]triazole as a white solid melting at 119-120° C.

MS: M=483.5 (ES+)

$^1$H-NMR(400 MHz, D$_6$-DMSO): δ=2.12 (s, 3H, CH$_3$), 3.81 (t, 2H, CH$_2$), 4.40 (s, 2H, CH$_{22}$), 4.58 (t, 2H, CH$_2$), 4.98 (s, 2H, CH$_2$), 6.80 (dd, 1H), 6.84(d, 1H), 7.13(d, 1H), 7.14 (d, 16.7 Hz, 1H), 7.21 (d, 2H), 7.31 (t, 74.5 Hz, 1H, CHF$_2$), 7.53 (d, 16.7 Hz, 1H), 7.71 (s, 1H), 7.79 (d, 2H), 8.07 (s, 1H), 8.18 (s, 1H).

Example 8

1-[2-(2-Methyl-4-{2-[2-(4-trifluoromethylsulfanyl-phenyl)-vinyl]-oxazol-4-ylmethoxy}-benzyloxy)-ethyl]-1H-[1,2,3]triazole A mixture of 201 mg (0.86 mmol) 3-methyl-4-(2-[1,2,3]triazol-1-yl-ethoxymethyl)-phenol and 169 mg (0.52 mmol) cesium carbonate in 10 ml 2-butanone was stirred at 60° C. for 30 minutes, then 275 mg (0.86 mmol) 4-chloromethyl-2-[2-(4-trifluoromethylsulfanyl-phenyl)-vinyl]-oxazole and 143 mg (0.86 mmol) potassium iodide were added and stirring was continued overnight. After evaporation, the residue was mixed with aqueous NaOH (1N) and extracted with ethyl acetate. The combined extracts were dried, evaporated and the product purified on silica (ethyl acetate) to yield 280 mg (63%) of the title as a white solid melting at 102° C.

MS: M=517.3 (ES+)

$^1$H-NMR(400 MHz. D$_6$-DMSO): δ=2.13 (s, 3H, CH$_3$), 3.82 (t, 2H, CH$_2$), 4.40 (s, 2H, CH$_2$), 4.58 (t, 2H, CH$_2$), 5.00 (s, 2H, CH$_2$), 6.75-6.88 (m, 2H), 7.13(d, 1H), 7.33 (d, 16.2 Hz, 1H), 7.60 (d, 16.7 Hz, 1H), 7.67-7.79 (m, 3H), 7.86 (d, 2H), 8.07 (s, 1H), 8.23 (s, 1H).

Example 9

1-[2-(2-Methyl-4-{2-[2-(4-trifluoromethoxy-phenyl)-vinyl]-oxazol-4-ylmethoxy}-benzyloxy)-ethyl]-1H-[1,2,3]triazole A mixture of 201 mg (0.86 mmol) 3-methyl-4-(2-[1,2,3]triazol-1-yl-ethoxymethyl)-phenol and 169 mg (0.52 mmol) cesium carbonate in 10 ml 2-butanone was stirred at 60° C. for 30 minutes, then 261 mg (0.86 mmol) 4-chloromethyl-2-[2-(4-trifluoromethoxy-phenyl)-vinyl]-oxazole and 143 mg (0.86 mmol) potassium iodide were added and stirring was continued overnight. After evaporation, the residue was mixed with aqueous NaOH (1N) and extracted with ethyl acetate. The combined extracts were dried, evaporated and the product purified on silica (ethyl acetate) to yield 208 mg (49%) of the title as a white solid melting at 84-85° C.

MS: M=501.6 (ES+)

$^1$H-NMR(400 MHz, D$_6$-DMSO): δ=2.12 (s, 3H, CH$_3$), 3.82 (t, 2H, CH$_2$), 4.40 (s, 2H, CH$_2$), 4.58 (t, 2H, CH$_2$), 4.99 (s, 2H, CH$_2$), 6.80 (d, 1H), 6.84 (s, 1H), 7.13(d, 1H), 7.21 (d, 16.7 Hz, 1H), 7.40 (d, 2H), 7.57 (d, 16.7 Hz, 1H), 7.71 (s, 1H), 7.86 (d, 3H), 8.07 (s, 1H), 8.21 (s, 1H).

Example 10

1-[2-(2-Fluoro-4-{2-[2-(4-trifluoromethoxy-phenyl)-vinyl]-oxazol-4-ylmethoxy}-benzyloxy)-ethyl]-1H-[1,2,3]triazole i) (4-allyloxy-2-fluoro-phenyl)-methanol 11.9 g (85.8 mmol) potassium carbonate and 0.357 g (2.15 mmol) potassium iodide were given to a solution of 6.10 g (42.9 mmol) 2-fluoro-4-hydroxymethylphenol and 20.8 g (172 mmol) allyl bromide in 250 ml 2-butanone and stirred for 32 h at 65° C. Solvents were distilled off and the residue distributed between ethyl acetate and 1 N sodium hydroxide. The organic layer was separated, dried and evaporated to give 4.27 g (55%) of (4-allyloxy-2-fluoro-phenyl)-methanol.

$^1$H-NMR(400 MHz, CDCl$_3$): δ=1.70(t, 1H, OH), 4.52(d, 2H, OC$\underline{H}_2$-vinyl), 4.67(d, 2H, CH$_2$OH), 5.31(d, 1H, =CH$_2$), 5.41(d, 1H, =CH$_2$), 6.02(m, 1H, C$\underline{H}$=CH$_2$), 6.63(d, 1H, 3-H), 6.70(d, 1H, 5-H), 7.29(d, 1H, 6-H).

ii) 1-allyloxy-3-fluoro-4-chloromethyl-benzene

A solution of 4.20 g (23.1 mmol) (4-allyloxy-2-fluoro-phenyl)-methanol in 80 ml dichloro-methane and 0.5 ml DMF was cooled to 0° C. 2.17 ml (3.57 g, 30.0 mmol) thionyl chloride were added slowly and then stirred for 1 h at room temperature. Dichloromethane was distilled off. The residue was taken up in 100 ml ethyl acetate and washed with concentrated sodium carbonate solution. The organic phase was dried and evaporated to give 4.47 g (97%) 1-allyloxy-3-fluoro-4-chloromethyl-benzene as colored oil.

$^1$H-NMR(400 MHz, CDCl$_3$): δ=4.52(d, 2H, OC$\underline{H}_2$-vinyl), 4.60(s, 2H, CH$_2$Cl), 5.31(d, 1H, =CH$_2$), 5.41(d, 1H, =CH$_2$), 6.03(m, 1H, C$\underline{H}$=CH$_2$), 6.64(d, 1H, 2-H), 6.69(d, 1H, 6-H), 7.29(d, 1H, 5-H).

iii) 1-[2-(4-allyloxy-2-fluoro-benzyloxy)-ethyl]-1H-[1,2,3]triazole 816 mg (32.3 mmol) 95% Sodium hydride were given at −50° C. to a solution of 4.32 g (21.5 mmol) 1-allyloxy-3-fluoro-4-chloromethyl-benzene and 2.51 g (22.2 mmol) 2-(1H-[1,2,3]-triazol-1-yl)-ethanol in 30 ml DMF. The mixture was allowed to warm slowly to r.t., stirred overnight and 10 ml water added. The mixture was extracted twice with ethyl acetate, and the combined organic phases dried over Na$_2$SO$_4$. Solvents were removed in vacuum to yield 6.18 g 1-[2-(4-allyloxy-2-fluoro-benzyloxy)-ethyl]-1H-[1,2,3]triazole yellow oil that was used without further purification.

$^1$H-NMR(400 MHz, CDCl$_3$): δ=3.84(t, 2H, C$\underline{H}$—CH$_2$-triazole), 4.48(s, 2H, OCH$_2$Ph), 4.52(d, 2H, OCH$_2$-vinyl) 4.58(t, CH$_2$-triazole), 5.25(d, 1H, =CH$_2$), 5.38(d, 1H, =CH$_2$), 6.06(m, 1H, C$\underline{H}$=CH$_2$), 6.62(d, 1H, 3-H), 6.68(d, 1H, 5-H), 7.14(t, 1H, 6-$\underline{H}$), 7.68(s, 1H, triazole), 7.69(s, 1H, triazole).

iv) 3-fluoro-4-(2-[1,2,3]triazol-1-yl-ethoxymethyl)-phenol

To a solution of 10.4 g (66.9 mmol) 1,3-dimethyl-pyrimidine-2,4,6-trione and 774 mg (0.67 mmol) tetrakis-(triphenylphosphine)-palladium in 100 ml dichloromethane was added dropwise a solution of 6.18 g (22.3 mmol) 1-[2-(4-allyloxy-2-fluoro-benzyloxy)-ethyl]-1H-[1,2,3]triazole in 30 ml dichloromethane and stirring was continued for 24 hours at 40° C. It was allowed to cool down over night. The reaction mixture was extracted with three 100 ml portions of sodium bicarbonate solution, the organic extract was dried, evaporated and purified by chromatography on silica (ethyl acetate/dichloromethane 3:7) to yield 2.97 g (56%) 3-fluoro-4-(2-[1,2,3]triazol-1-yl-ethoxymethyl)-phenol as oil.

$^1$H-NMR(400 MHz, D$_6$-DMSO): δ=3.79(t, 2H, OC$\underline{H}_2$—CH$_2$-triazole), 4.38(s, 2H, OC$\underline{H}_2$Ph), 4.56(t, 2H, CH$_2$-triazole), 6.53(d, 1H, 2-H), 6.56(d, 1H, 6-H), 7.11(d, 1H, 5-H), 7.71(s, 1H, triazole), 8.05(s, 1H, triazole), 9.91(s, 1H, OH).

v) 1-[2-(2-fluoro-4-{2-[2-(E)-(4-trifluoromethoxy-phenyl)-vinyl]-oxazol-4-ylmethoxy}-benzyloxy)-ethyl]-1H-[1,2,3]triazole A solution of 201 mg (0.847 mmol) 3-Fluoro-4-(2-[1,2,3]triazol-1-yl-ethoxylmethyl)-phenol in 5 ml dimethylformamide was treated with 22.5 mg (0.890 mmol) 95% sodium hydride and stirred at room temperature for 20 min, then 257 mg (0.847 mmol) 4-chloromethyl-2-[2-(4-trifluoromethoxy-phenyl)-vinyl]-oxazole were added and stirring continued for 14 h. After addition of water, the precipitate was isolated, washed thoroughly with water, twice with ether and dried to give 1-[2-(2-fluoro-4-{2-[2-(E)-(4-trifluoromethoxy-phenyl)-vinyl]-oxazol-4-ylmethoxy}-benzyloxy)-ethyl]-1H-[1,2,3]triazole.

$^1$H-NMR(400 MHz, D$_6$-DMSO): δ=3.83(t, 2H, C$\underline{H}_2$—CH$_2$-triazole), 4.45(s, 2H, OCH$_2$-Ph), 4.58(t, 2H, CH$_2$-triazole), 5.04(s, 2H, OCH$_2$-oxazole), 6.85(d, 1H, 5-H), 6.94(d, 1H, 3-H), 7.21(d, 1H, vinyl-H), 7.26(d, 1H, 6-H), 7.41(d, 2H, ArOCF$_3$), 7.57(d, 1H, vinyl-H), 7.71(s, 1H, triazole), 7.87(d, 2H, ArOCF$_3$), 8.07(s, 1H, triazole), 8.24(s, 1H, oxazole).

Unless stated to the contrary, all compounds in the examples were prepared and characterized as described. All ranges recited herein encompass all combinations and sub-combinations within such ranges. All patents and publications cited herein are hereby incorporated by reference in their entirety.

What is claimed is:
1. A compound according to, formula (I),

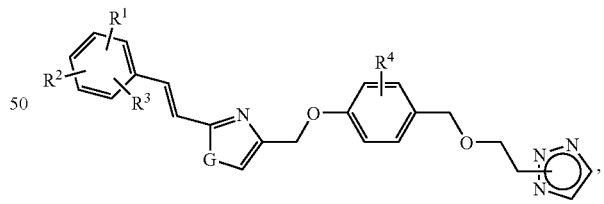

formula I wherein:
G is oxygen or sulfur;
R$^4$ is selected from the group consisting of:
(a) hydrogen;
(b) C$_1$-C$_3$ alkyl;
(c) C$_1$-C$_3$ alkoxy; and
(d) halogen;
and, either:
(A) R$^1$ is selected from the group consisting of:
(a) —O-alkyl, wherein the alkyl group is optionally substituted with one or more halogen atoms;

(b) —S-alkyl, wherein the alkyl group is optionally substituted with one or more halogen atoms; and
(c) —NH-alkyl, wherein the alkyl group is optionally substituted with one or more halogen atoms;

$R^2$ is hydrogen or halogen; and
$R^3$ is hydrogen;
or, alternatively,
(B) wherein $R^1$ and $R^2$, together with the carbon atoms to which they are attached, form a 5 or 6 membered heterocyclic ring, being optionally once or several times substituted with halogen, and $R^3$ is hydrogen or halogen;
G is oxygen or sulfur;
or a pharmaceutically acceptable salt or ester thereof.

2. A compound according to claim 1, wherein:
$R^1$ is selected from the group consisting of: —O—$CF_3$, —O—$CHF_2$, and —S—$CF_3$;
$R^2$ is hydrogen;
$R^3$ is hydrogen;
$R^4$ is hydrogen; and
G is oxygen.

3. A compound according to claim 2 selected from the group consisting of:
1-[2-(4-{2-[2-(E)-(4-Trifluoromethylsulfanyl-phenyl)-vinyl]-oxazol-4-ylmethoxy}-benzyloxy)-ethyl]-1H-[1,2,3]triazole;
2-[2-(4-{2-[2-(E)-(4-Trifluoromethoxy-phenyl)-vinyl]-oxazol-4-ylmethoxy}-benzyloxy)-ethyl]-2H-[1,2,3]triazole;
4-[2-(4-{2-[2-(E)-(4-Trifluoromethoxy-phenyl)-vinyl]-oxazol-4-ylmethoxy}-benzyloxy)-ethyl]-1H-[1,2,3]-triazole;
1-[2-(4-{2-[2-(E)-(4-Trifluoromethoxy-phenyl)-vinyl]-oxazol-4-ylmethoxy}-benzyloxy)-ethyl]-1H-[1,2,3]triazolium methanesulfonate;
1-[2-(4-{2-[2-(E)-(4-Trifluoromethoxy-phenyl)-vinyl]-oxazol-4-ylmethoxy}-benzyloxy)-ethyl]-1H-[1,2,3]triazolium p-toluenesulfonate;
1-[2-(4-{2-[2-(E)-(4-Trifluoromethoxy-phenyl)-vinyl]-oxazol-4-ylmethoxy}-benzyloxy)-ethyl]-1H-[1,2,3]triazolium chloride;
1-[2-(4-{2-[2-(E)-(4-Trifluoromethoxy-phenyl)-vinyl]-oxazol-4-ylmethoxy}-benzyloxy)-ethyl]-1H-[1,2,3]triazole; and
1-[2-(4-{2-[2-(E)-(4-Difluoromethoxy-phenyl)-vinyl]-oxazol-4-ylmethoxy}-benzyloxy)-ethyl]-1H-[1,2,3]triazole.

4. A compound according to claim 1, wherein:
$R^1$ is selected from the group consisting of: —O—$CF_3$; —O—$CHF_2$; and —S—$CF_3$;
$R^2$ is halogen;
$R^3$ is hydrogen; and
$R^4$ is hydrogen.

5. A compound according to claim 4 selected from the group consisting of:
1-[2-(4-{2-[2-(E)-(2-Fluoro-4-trifluoromethoxy-phenyl)-vinyl]-oxazol-4-ylmethoxy}-benzyloxy)-ethyl]-1H-[1,2,3]triazole; and
1-[2-(4-{2-[2-(E)-(2-Fluoro-4-trifluoromethylsulfanyl-phenyl)-vinyl]-oxazol-4-ylmethoxy}-benzyloxy)-ethyl]-1H-[1,2,3]triazole.

6. A compound according to claim 1, wherein:
$R^1$ and $R^2$, together with the carbon atoms to which they are attached form 2,2-Difluoro-benzo[1,3]dioxolyl;
$R^3$ is hydrogen; and
$R^4$ is hydrogen.

7. A compound according to claim 6, wherein the compound is:
1-[2-(4-{2-[2-(E)-(2,2-Difluoro-benzo[1,3]dioxol-5-yl)-vinyl]-oxazol-4-ylmethoxy}benzyloxy)-ethyl]-1H-[1,2,3]triazole.

8. A compound according to claim 1, wherein:
$R^1$ and $R^2$, together with the carbon atoms to which they are attached, form 2,2-Difluoro-benzo[1,3]dioxolyl;
$R^3$ is halogen; and
$R^4$ is hydrogen.

9. A compound according to claim 8, wherein the compound is:
1-[2-(4-{2-[2-(E)-(2,2,6-Trifluoro-benzo[1,3]dioxol-5-yl)-vinyl]-oxazol-4-ylmethoxy}-benzyloxy)-ethyl]-1H-[1,2,3]triazole.

10. A compound according to claim 1 wherein said compound is a compound of formula I-A, formula I-A wherein:
G is oxygen or sulfur;
$R^4$ is selected from the group consisting of: fluorine, methyl, and methoxy;
and, either:
(A) $R^1$ is selected from the group consisting of:
(a) —O-alkyl, wherein the alkyl group is optionally substituted with one or more halogen atoms;
(b) —S-alkyl, wherein the alkyl group is optionally substituted with one or more halogen atoms;
(c) —NH-alkyl, wherein the alkyl group is optionally substituted with one or more halogen atoms;
$R^2$ is hydrogen or halogen; and
$R^3$ is hydrogen;
or, alternatively,
(B) $R^1$ and $R^2$, together with the carbon atoms to which they are attached, form a 5 or 6 membered heterocyclic ring, being optionally once or several times substituted with halogen, and $R^3$ is hydrogen or halogen;
or a pharmaceutically acceptable salt or ester thereof.

11. A compound according to claim 10 selected from the group consisting of:
1-[2-(2-Fluoro-4-{2-[2-(E)-(4-difluoromethoxy-phenyl)-vinyl]-oxazol-4-ylmethoxy}-benzyloxy)-ethyl]-1H-[1,2,3]-triazole;
1-[2-(2-Methyl-4-{2-[2-(E)-(4-difluoromethoxy-phenyl)-vinyl]-oxazol-4-ylmethoxy}-benzyloxy)-ethyl]-1H-[1,2,3]-triazole;
1-[2-(2-Methoxy-4-{2-[2-(E)-(4-difluoromethoxy-phenyl)-vinyl]-oxazol-4-ylmethoxy}-benzyloxy)-ethyl]-1H-[1,2,3]-triazole;
1-[2-(2-Fluoro-4-{2-[2-(E)-(4-trifluoromethoxy-phenyl)-vinyl]-oxazol-4-ylmethoxy)}-benzyloxy)-ethyl]-1H-[1,2,3]-triazole;
1-[2-(2-Methyl-4-{2-[2-(E)-(4-trifluoromethoxy-phenyl)-vinyl]-oxazol-4-ylmethoxy}-benzyloxy)-ethyl]-1H-[1,2,3]-triazole;

1-[2-(2-Methoxy-4-{2-[2-(E)-(4-trifluoromethoxy-phenyl)-vinyl]-oxazol-4-ylmethoxy}-benzyloxy)-ethyl]-1H-[1,2,3]-triazole;

1-[2-(2-Fluoro-4-{2-[2-(E)-(4-trifluoromethylsulfanyl-phenyl)-vinyl]-oxazol-4-ylmethoxy}-benzyloxy)-ethyl]-1H-[1,2,3]-triazole;

1-[2-(2-Methyl-4-{2-[2-(E)-(4-trifluoromethylsulfanyl-phenyl)-vinyl]-oxazol-4-ylmethoxy}-benzyloxy)-ethyl]-1H-[1,2,3]-triazole; and 1-[2-(2-Methoxy-4-{2-[2-(E)-(4-trifluoromethylsulfanyl-phenyl)-vinyl]-oxazol-4-ylmethoxy}-benzyloxy)-ethyl]-1H-[1,2,3-triazole.

12. A compound according to claim 10, wherein:
G is oxygen;
$R^3$ is hydrogen;
$R^4$ is hydrogen, $C_1$-$C_3$ alkyl, or fluorine;
and, either:
(A) $R^1$ is selected from the group consisting of:
  (a) —O-alkyl; wherein the alkyl group is optionally substituted with one or more fluorine atoms; and
  (b) —S-alkyl; wherein the alkyl group is optionally substituted with one or more fluorine atoms; and
$R^2$ is hydrogen;
or, alternatively,
(B) $R^1$ and $R^2$, together with the carbon atoms to which they are attached, form 2,2-Difluoro-benzo[1,3]dioxolyl.

13. A compound according to claim 1 wherein said compound is a compound of formula I-B,

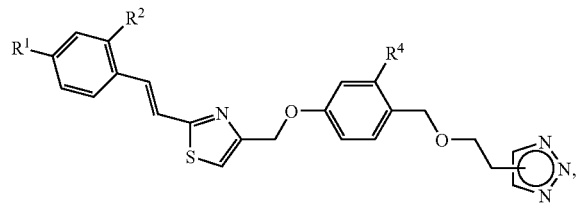

formula I-B wherein:
$R^1$ is —O—$CF_3$ or —O—$CHF_2$;
$R^2$ is hydrogen or halogen; and
$R^4$ is selected from the group consisting of: hydrogen, methyl, methoxy, and fluorine;
or a pharmaceutically acceptable salt or ester thereof.

14. A compound according to claim 13 selected from the group consisting of:

1-[2-(4-{2-[2-(E)-(4-trifluoromethoxy-phenyl)-vinyl]-thiazol-4-ylmethoxy}-benzyloxy)-ethyl]-1H-[1,2,3] triazole;

1-[2-(4-{2-[2-(E)-(4-difluoromethoxy-phenyl)-vinyl]-thiazol-4-ylmethoxy}-benzyloxy)-ethyl]-1H-[1,2,3]-triazole;

1-[2-(2-Fluoro-4-{2-[2-(E)-(4-difluoromethoxy-phenyl)-vinyl]-thiazol-4-ylmethoxy}-benzyloxy)-ethyl]-1H-[1,2,3-triazole;

1-[2-(2-Methyl-4-{2-[2-(E)-(4-difluoromethoxy-phenyl)-vinyl]-thiazol-4-ylmethoxy}-benzyloxy)-ethyl]-1H-[1,2,3-triazole;

1-[2-(2-Methoxy-4-{2-[2-(E)-(4-difluoromethoxy-phenyl)-vinyl]-thiazol-4-ylmethoxy}-benzyloxy)-ethyl]-1H-[1,2,3]-triazole;

1-[2-(2-Fluoro-4-{2-2-(E)-(4-trifluoromethoxy-phenyl)-vinyl]-thiazol-4-ylmethoxy}-benzyloxy)-ethyl]-1H-[1,2,3-triazole;

1-[2-(2-Methyl-4-{2-[2-(E)-(4-trifluoromethoxy-phenyl)-vinyl]-thiazol-4-ylmethoxy}-benzyloxy)-ethyl]-1H-[1,2,3]-triazole;

1-[2-(2-Methoxy-4-{2-2-(E)-(4-trifluoromethoxy-phenyl)-vinyl]-thiazol-4-ylmethoxy}-benzyloxy)-ethyl]-1H-[1,2,3-triazole; and 4-[2-(4-{2-[2-(E)-(4-trifluoromethoxy-phenyl)-vinyl]-thiazol-4-ylmethoxy}-benzyloxy)-ethyl]-1H-[1,2,3]-triazole.

15. A compound according to claim 13 selected from the group consisting of:

1-[2-(4-{2-[2-(E)-(4-trifluoromethoxy-phenyl)-vinyl]-thiazol-4-ylmethoxy}-benzyloxy)-ethyl]-1H-[1,2,3] triazolium methanesulfonate;

1-[2-(4-{2-[2-(E)-(4-trifluoromethoxy-phenyl)-vinyl]-thiazol-4-ylmethoxy}-benzyloxy)-ethyl]-1H-[1,2,3] triazolium p-toluenesulfonate; and 1-[2-(4-{2-[2-(E)-(4-trifluoromethoxy-phenyl)-vinyl]-thiazol-4-ylmethoxy}-benzyloxy)-ethyl]-1H-[1,2,3] triazolium chloride.

16. The process for the manufacture of a compound according to claim 1, wherein:
the compound of formula (V)

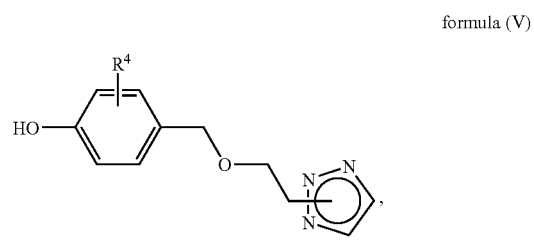

formula (V)

wherein $R^4$ is defined in claim 1,
is reacted with a compound of formula (IV)

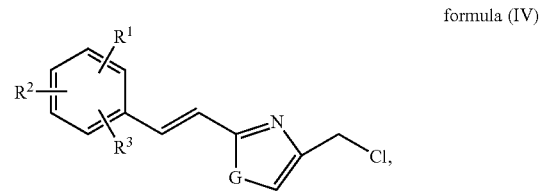

formula (IV)

wherein $R^1$, $R^2$, $R^3$ and G are as defined in claim 1, to give the respective compound of formula (I).

17. A pharmaceutical composition comprising a therapeutically effective amount of the compound of claim 1 and a pharmaceutically acceptable carrier.

* * * * *